US011236030B2

(12) United States Patent
Usui et al.

(10) Patent No.: US 11,236,030 B2
(45) Date of Patent: Feb. 1, 2022

(54) METHOD FOR PRODUCING FLUOROOLEFIN

(71) Applicant: DAIKIN INDUSTRIES, LTD., Osaka (JP)

(72) Inventors: Takashi Usui, Osaka (JP); Tsubasa Nakaue, Osaka (JP); Takehiro Chaki, Osaka (JP); Yuzo Komatsu, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 17/052,389

(22) PCT Filed: Apr. 22, 2019

(86) PCT No.: PCT/JP2019/017000
§ 371 (c)(1),
(2) Date: Nov. 2, 2020

(87) PCT Pub. No.: WO2019/216175
PCT Pub. Date: Nov. 14, 2019

(65) Prior Publication Data
US 2021/0253502 A1 Aug. 19, 2021

(30) Foreign Application Priority Data

May 8, 2018 (JP) .............................. JP2018-090202
Aug. 28, 2018 (JP) .............................. JP2018-158927

(51) Int. Cl.
*C07C 17/25* (2006.01)
*B01J 21/04* (2006.01)
*B01J 23/26* (2006.01)
*B01J 35/10* (2006.01)
*B01J 37/08* (2006.01)
*B01J 37/26* (2006.01)

(52) U.S. Cl.
CPC ............... *C07C 17/25* (2013.01); *B01J 21/04* (2013.01); *B01J 23/26* (2013.01); *B01J 35/1014* (2013.01); *B01J 37/082* (2013.01); *B01J 37/26* (2013.01)

(58) Field of Classification Search
CPC .. B01J 23/26; B01J 37/26; B01J 21/04; C07C 17/25; C07C 21/18; C07C 17/354
See application file for complete search history.

(56) References Cited

U.S. PATENT DOCUMENTS

| | | | |
|---|---|---|---|
| 3,432,562 A | 3/1969 | Gardner | |
| 5,059,729 A | 10/1991 | Gervasutti | |
| 5,208,396 A * | 5/1993 | Anton | C07C 17/00 570/170 |
| 2010/0185029 A1* | 7/2010 | Elsheikh | C07C 21/18 570/157 |
| 2018/0093935 A1* | 4/2018 | Chaki | C07C 21/06 |

FOREIGN PATENT DOCUMENTS

| | | |
|---|---|---|
| EP | 0 234 002 | 9/1987 |
| JP | 62-169737 | 7/1987 |
| JP | 01-287044 | 11/1989 |
| JP | 10-505337 | 5/1998 |
| JP | 2013-525487 | 6/2013 |
| JP | 2013-237624 | 11/2013 |
| JP | 2016-56132 | 4/2016 |
| WO | 96/05157 | 2/1996 |
| WO | 2011/140013 | 11/2011 |
| WO | 2016/159205 | 10/2016 |
| WO | 2017/104828 | 6/2017 |

OTHER PUBLICATIONS

International Search Report dated Jul. 16, 2019 in International (PCT) Application No. PCT/JP2019/017000.

* cited by examiner

*Primary Examiner* — Jafar F Parsa
(74) *Attorney, Agent, or Firm* — Wenderoth, Lind & Ponack, L.L.P.

(57) ABSTRACT

The present disclosure provides a method for producing fluoroolefin represented by formula (1): $CX^1X^2=CX^3X^4$, wherein $X^1$, $X^2$, $X^3$, and $X^4$ are the same or different, and represent a hydrogen atom or a fluorine atom, with high selectivity. Specifically, the present disclosure is a method for producing a fluoroolefin represented by formula (1) described above, the method comprising a dehydrofluorination step of bringing a fluorocarbon represented by formula (2): $CX^1X^2FCX^3X^4H$, wherein $X^1$, $X^2$, $X^3$, and $X^4$ are as defined above, into contact with a metal catalyst to perform dehydrofluorination, the dehydrofluorination step being performed in the gas phase in the presence of water, the concentration of the water being less than 500 ppm relative to the fluorocarbon represented by formula (2).

13 Claims, No Drawings

METHOD FOR PRODUCING FLUOROOLEFIN

TECHNICAL FIELD

The present disclosure relates to a method for producing fluoroolefin.

BACKGROUND ART

Recently, 1,1-difluoroethylene (HFO-1132a) represented by $CF_2=CH_2$, 1,2-difluoroethylene (HFO-1132) represented by $CFH=CFH$, and the like are considered to be promising refrigerant compounds that have a low global warming potential (GWP).

For example, Patent Literature 1 discloses a method for producing HFO-1132a by bringing 1,1,1-trifluoroethane (HFC-143a) or 1,1,2-trifluoroethane (HFC-143) into contact with a metal catalyst to perform a dehydrofluorination reaction.

Patent Literature 2 discloses a method for producing HFO-1132, comprising the step of subjecting dichlorofluoromethane (HCFC-21) to thermal decomposition to obtain 1,2-dichloro-1,2-difluoroethylene (CFC-1112), and the step of hydrogenating the obtained CFC-1112.

Patent Literature 3 discloses a method for producing HFO-1132 by reacting 1-chloro-1,2-difluoroethylene (HCFO-1122a) with hydrogen in the gas phase in the presence of a hydrogenation catalyst.

CITATION LIST

Patent Literature

PTL 1: WO2017/104828
PTL 2: JP2013-237624A.
PTL 3: JP2016-056132A

SUMMARY OF INVENTION

Technical Problem

An object of the present disclosure is to produce fluoroolefin represented by formula (I): $CX^1X^2=CX^3X^4$, wherein $X^2$, $X^3$, and $X^4$ are the same or different, and represent a hydrogen atom or a fluorine atom, with high selectivity.

Solution to Problem

The present disclosure is the following.
Item 1. A method for producing a fluoroolefin represented by formula (1): $CX^1X^2=CX^3X^4$, wherein $X^1$, $X^2$, $X^3$, and $X^4$ are the same or different, and represent a hydrogen atom or a fluorine atom,
the method comprising a dehydrofluorination step of bringing a fluorocarbon represented by formula (2): $CX^1X^2FCX^3X^4H$, wherein $X^1$, $X^2$, $X^3$, and $X^3$ are as defined above, into contact with a metal catalyst to perform dehydrofluorination,
the dehydrofluorination step being performed in the gas phase in the presence of water,
the concentration of the water being less than 500 ppm relative to the fluorocarbon represented by formula (2).
Item 2. The production method according to Item 1, wherein the fluoroolefin represented by formula (1) is at least one member selected from the group consisting of 1,2-difluoroethylene (HFO-1132), 1,1-difluoroethylene (HFO-1132a), and trifluoroethylene (HFO-1123).
Item 3. The production method according to Item 1 or 2, wherein the fluorocarbon represented by formula (2) is at least one member selected from the group consisting of 1,1,1-trifluoroethane (HFC-143a), 1,1,2-trifluoroethane (HFC-143), 1,1,2,2-tetrafluoroethane (HFC-134), and 1,1,1,2-tetrafluoroethane (HFC-134a).
Item 4. The production method according to any one of Items 1 to 3, wherein the dehydrofluorination step is performed in the presence of an oxidizing agent.
Item 5. The production method according to Item 4, wherein the oxidizing agent is oxygen.
Item 6. The production method according to Item 5, wherein the concentration of the oxygen is 0.01 to 21 mol % relative to the fluorocarbon represented by formula (2).
Item 7. The production method according to any one of Items 1 to 6, wherein the metal catalyst is at least one member selected from the group consisting of chromium oxide, fluorinated chromium oxide, chromium fluoride, aluminum oxide, fluorinated aluminum oxide, aluminum fluoride, iron oxide, fluorinated iron oxide, iron fluoride, nickel oxide, fluorinated nickel oxide, nickel fluoride, magnesium oxide, fluorinated magnesium oxide, and magnesium fluoride.
Item 8. The production method according to any one of Items 1 to 7, wherein the dehydrofluorination step is performed at a temperature of 300 to 600° C.
Item 9. The production method according to any one of Items 1 to 8, wherein, in the dehydrofluorination step, the contact time ($W/F_0$) between the fluorocarbon represented by formula (2) and the metal catalyst is 10 g·sec/ML to 200 g·sec/mL.
Item 10. The production method according to any one of Items 1 to 9, wherein the dehydrofluorination step is performed in the presence of an inert gas and/or hydrogen fluoride.
Item 11. The production method according to Item 10, wherein the dehydrofluorination step is performed in the presence of an inert gas, and the inert gas is at least one member selected from the group consisting of nitrogen, helium, argon, and carbon dioxide.
Item 12. The production method according to any one of Items 1 to 11, comprising a hydrogenation step of subjecting a fluoroolefin represented by formula (3): $CX^5X^6=CX^7X^8$, wherein $X^5$, $X^6$, $X^7$, and $X^8$ are the same or different, and represent a hydrogen atom, a fluorine atom, or a chlorine atom; and at least one of $X^5$, $X^6$, $X^7$, and $X^8$ represents a fluorine atom, to a hydrogenation reaction to obtain the fluorocarbon represented by formula (2).
Item 13. The production method according to Item 12, wherein the fluoroolefin represented by formula (3) is chlorotrifluoroethylene (CTFE).

Advantageous Effects of Invention

According to the production method of the present disclosure, fluoroolefin represented by formula (1) above can be produced with high selectivity.

Description of Embodiments

As a result of extensive research, the present inventors found that, by a reaction between a raw material compound and a metal catalyst in the gas phase in the presence of a very small amount of water, fluoroolefin represented by formula (1) above can be produced with high selectivity.

The present disclosure was completed as a result of further research based on the above findings. The present disclosure includes the following embodiments.

In the method for producing fluoroolefin (in the present disclosure, sometimes referred to as a "target compound") represented by formula (1): $CX^1X^2=CX^3X^4$, wherein $X^1$, $X^2$, $X^3$, and $X^4$ are the same or different, and represent a hydrogen atom or a fluorine atom, with a proviso that at least one of $X^1$, $X^2$, $X^3$, and $X^4$ is a fluorine atom) comprises a dehydrofluorination step of bringing a fluorocarbon (in the present disclosure, sometimes referred to as a "raw material compound") represented by formula (2): $CX^1X^2FCX^3X^4H$, wherein $X^1$, $X^2$, $X^3$, and $X^4$ are as defined above, into contact with a metal catalyst to perform dehydrofluorination.

In the present disclosure, the dehydrofluorination step is performed in the gas phase in the presence of water.

In the present disclosure, the concentration of the water is less than 500 ppm relative to the fluorocarbon represented by formula (2).

In the present disclosure, by satisfying the above requirements, high conversion of the raw material compound is achieved, and the target compound can be obtained with high selectivity.

In the present disclosure, the concentration of water means the water concentration relative to the raw material compound, and the unit "ppm" means ppm by mass.

In the present disclosure, "conversion" refers to the ratio (mol %) of the total molar amount of compounds other than the raw material compound contained in the gas flowing out of the reactor outlet to the molar amount of the raw material compound supplied to the reactor, and "selectivity" refers to the ratio (mol %) of the total molar amount of the target compound contained in the flowing gas to the total molar amount of compounds other than the raw material compound contained in the gas flowing out of the reactor.

Raw Material Compound

In the present disclosure, the raw Material compound is a fluorocarbon represented by formula (2): $CX^1X^2FCX^3X^4H$, wherein $X^1$, $X^2$, $X^3$, and $X^4$ are as defined above.

The fluorocarbon represented by formula (2) above is preferably at least one member selected from the group consisting of 1,1,1-trifluoroethane (HFC-143a), 1,1,2-trifluoroethane (HFC-143), 1,1,2,2-tetrafluoroethane (HFC-134), and 1,1,1,2-tetrafluoroethane (HFC-134a). Of these, 1,1,2-trifluoroethane (HFC-143) is more preferable.

HFC-143 can be produced by a method of reducing chlorotrifluoroethylene (CTFE) with hydrogen in the presence of a palladium catalyst or a platinum catalyst. Additionally, HFC-143 can be produced by a method of reducing HFO-1123 or CFC-113 (1,1,2-trichloro-1,2,2-trifluoroethane) with hydrogen in the presence of palladium. Moreover, HFC-143 can be produced by a method of fluorinating 1,1,2 trichloroethane with mercury oxide in the presence of hydrogen fluoride.

Dehydrofluorination Step

In the dehydrofluorination step in the present disclosure, it is essential to bring the raw material compound into contact with a metal catalyst in the gas phase in the presence of water to perform dehydrogenation.

For example, a dehydrofluorination reaction when HFC-134 is used as a raw material compound is performed according to the following reaction formula.
$CF_2HCF_2H \rightarrow CF_2=CHF + HF$ (HFC-134) (HFO-1123)

The metal catalyst used in this step is preferably at least one member selected from the group consisting of chromium oxide, fluorinated chromium oxide, chromium fluoride, aluminum oxide, fluorinated aluminum oxide, aluminum fluoride, iron oxide, fluorinated iron oxide, iron fluoride, nickel oxide, fluorinated nickel oxide, nickel fluoride, magnesium oxide, fluorinated magnesium oxide, and magnesium fluoride. Of these, from the viewpoint of improving the conversion of the raw material compound and obtaining the target compound with high selectivity, chromium oxide, fluorinated chromium oxide, aluminum oxide, and fluorinated aluminum oxide are more preferable.

In this step, when the raw material compound is brought into contact with the metal catalyst in the gas phase in the presence of water, it is preferable to bring the metal catalyst in a solid state (solid phase) into contact with the raw material compound.

The specific surface area of the metal catalyst Measured by the BET method (also referred to below as "BET specific Surface area") is usually 10 to 400 $M^2/g$, preferably 20 to 375 $m^2/g$, and more preferably 30 to 350 $m^2/g$. When the BET specific surface area of the metal catalyst is in the above range, the density of the particles of the metal catalyst is not significantly small, so the conversion of the raw material compound can be improved, and the target compound can be obtained with high selectivity.

The metal catalyst is preferably supported on a carrier. Examples of the carrier include carbon, alumina ($Al_2O_3$), zirconia ($ZrO_2$), silica ($SiO_2$), titania ($TiO_2$), and the like. As carbon, activated carbon, amorphous carbon, graphite, diamond, or the like can be used.

Chromium oxide and fluorinated chromium oxide will be specifically described as examples of the catalyst used in the present disclosure.

When the chromium oxide is, for example, represented by $Cr_2O_3 \cdot nH_2O$, the value n is preferably 3 or less, and more preferably 1 to 1.5.

The chromium oxide is represented by a composition formula $CrO_m$, wherein m is generally $1.5<m<3$, and the fluorinated chromium oxide used as a catalyst can be prepared by fluorinating the chromium oxide. Examples of fluorination include fluorination by hydrogen fluoride (HF), fluorination by fluorocarbon, and the like.

Fluorinated chromium oxide used as a catalyst can be obtained, for example, by the method described in Japanese Patent No. 3412165. Below are shown examples of a method for preparing chromium oxide or fluorinated chromium oxide used as a catalyst.

First, a chromium hydroxide precipitate is obtained by mixing an aqueous solution of a chromium salt (chromium nitrate, chromium chloride, chrome alum, chromium sulfate, or the like) with aqueous ammonia. For example, 10% aqueous ammonia can be added dropwise to a 5.7% aqueous solution of chromium nitrate in an amount of 1 to 1.2 equivalents. The physical properties of chromium hydroxide can be controlled by the reaction rate of the precipitation reaction at this time. The reaction rate is preferably fast. The reaction rate depends on the reaction solution temperature, ammonia water mixing method (mixing speed), and stirring condition.

The precipitate of chromium hydroxide is filtered, washed, and then dried. Drying is preferably carried cut, for example, in air at 70 to 200° C. for 1 to 100 hours. More preferably, the drying is performed in air at 120° C. for 12 hours.

In the present disclosure, the catalyst after drying is chromium hydroxide. The catalyst after drying is crushed. The precipitation reaction rate is adjusted so that the crushed product (the particle size is 1000 μm or less; products having a particle size of 46 to 1000 μm: 95%) has a powder density of 0.6 to 1.1 g/ml, and preferably 0.6 to 1.0 g/ml. When the powder density is within such a range, the strength of the pellet and the activity of the catalyst are excellent.

3 wt % of graphite is mixed with the powder of the chromium hydroxide, and pellets are formed with a tableting machine. Each pellet has, for example, a diameter of 3.0 mm and a height of 3.0 mm. The crush strength (pellet strength) of the pellet is preferably 210±40 kg/cm$^2$.

If the pellet strength is too high, the gas contact efficiency is reduced, which decreases the catalytic activity and allows the pellets to easily crack. In contrast, if the pellet strength is too low, the pellets are easily pulverized and are difficult to handle.

The formed catalyst is calcined in an inert atmosphere Such as a nitrogen stream to obtain amorphous chromium oxide. The calcination temperature is preferably 360° C. or higher. If the calcination temperature is too high, chromium oxide will crystallize. It is thus desirable to raise the calcination temperature to the extent that crystallization can be avoided. The calcination is preferably performed at 380 to 460° C. for 1 to 5 hours, more preferably at 380 to 420° C. for 2 hours.

Fluorinated chromium oxide can then be obtained by subjecting the chromium oxide to fluorination with hydrogen fluoride (HF treatment). The fluorination temperature is preferably a temperature at which the produced water does not condense (for example, 150° C. at 1 atm), and the upper limit is preferably a temperature at which the catalyst does not crystallize due to reaction heat. The fluorination temperature is preferably, for example, 100 to 460° C. The pressure of the fluorination is preferably the pressure used in the catalytic reaction.

In the present disclosure, it is particularly preferable to use a highly fluorinated chromium Oxide catalyst containing a large amount of fluorine. The highly fluorinated chromium oxide catalyst can be obtained by fluorinating chromium oxide at a higher temperature than usual for a long period of time.

The highly fluorinated chromium oxide catalyst preferably has a fluorine content of 30 mass % or more, and more preferably 30 to 45 mass %. The fluorine content can be measured by change in mass of the catalyst or a general chromium oxide quantitative analysis method.

The dehydrofluorination reaction in this step is preferably performed in the presence of an oxidizing agent.

The oxidizing agent used in this step is preferably oxygen, chlorine, bromine, or iodine because high conversion of the raw material compound is attained and the target compound can be obtained with high selectivity. Among these oxidizing agents, oxygen is more preferable.

In the present disclosure, the concentration of the oxidizing agent is preferably 0.01 to 21 mol % relative to the raw material compound. The concentration of the oxidizing agent is preferably 1 to 20 mol %, more preferably 5 to 18 mol %, and particularly preferably 7.5 to 16 mol % relative to the raw material compound because conversion of the raw material compound can be further improved and the target compound can be obtained with higher selectivity.

The lower limit of the reaction temperature in the dehydrofluorination reaction is preferably 300° C., more preferably 320° C., even more preferably 340° C., and particularly preferably 350° C., from the viewpoint of more efficiently promoting the dehydrofluorination reaction and suppressing the decrease in conversion.

The upper limit of the reaction temperature in the dehydrofluorination reaction is preferably 600° C., more preferably 550° C., even more preferably 500° C., and particularly preferably 450° C., from the viewpoint of more efficiently promoting the dehydrofluorination reaction and suppressing the decrease in selectivity caused by decomposition or polymerization of the reaction product.

Regarding the time of the dehydrofluorination reaction, an increase in the contact time (W/F$_0$) (W: weight (g) of the metal catalyst; F$_0$: flow rate of the raw material compound (mL/sec)) of the raw material compound and the metal catalyst can raise the conversion of the raw material compound; however, the amount of the metal catalyst is increased, which requires large equipment and is thus inefficient.

Therefore, regarding the time of the dehydrofluorination reaction, to improve the conversion of the raw material compound and reduce equipment costs, the contact time (W/F$_0$) of the raw material compound and the metal catalyst is preferably 10 g·sec/ml to 200 g·sec/ml, more preferably 20 g·sec/ml to 175 g·sec/ml, even more preferably 30 g·sec/ml to 150 g·sec/ml, and particularly preferably 40 g·sec/ml to 125 g·sec/ml.

The contact time of the raw material compound and the metal catalyst means the time in which the raw material compound is in contact with the metal catalyst.

From the viewpoint of more efficiently advancing the dehydrofluorination reaction, the reaction pressure in the dehydrofluorination reaction is preferably −0.05 to 2 MPa, more preferably −0.01 to 1 MPa, and even more preferably atmospheric pressure to 0.5 MPa. In the present disclosure, gauge pressure is used unless otherwise specified.

In the dehydrofluorination reaction, the shape and the structure of the reactor used for bringing the raw material compound into contact with the metal catalyst to perform reaction is not limited as long as the reactor can withstand the above temperature and pressure. Examples of the reactor include vertical reactors, horizontal reactors, multi-tube reactors, and the like. Examples of materials for the reactor include glass, stainless steel, iron, nickel, iron-nickel alloys, and the like.

The dehydrofluorination reaction can be performed either in batch mode or in flow mode in which a raw material compound is continuously fed to a reactor and the target compound is continuously withdrawn from the reactor. When the target compound stays in the reactor, the dehydrofluorination reaction can further proceed. In view of this, the dehydrofluorination reaction is preferably performed in flow mode.

The atmosphere at which the dehydrofluorination reaction is performed is preferably in the presence of inert gas and/or hydrogen fluoride from the viewpoint of suppressing the deterioration of a metal catalyst. The inert gas is preferably at least one member selected from the group consisting of nitrogen, helium, argon, and carbon dioxide. Among these inert gases, nitrogen is more preferable from the viewpoint of cost reduction. The concentration of the inert gas is preferably 0 to 50 mol % of gas components to be introduced into the reactor.

In the present disclosure, because the concentration of water is less than 500 ppm relative to the raw material compound, the conversion of the raw material compound is increased, and the target compound can be obtained with high selectivity.

In the present disclosure, the upper limit of the concentration of water is preferably 300 ppm, more preferably 100 ppm, even more preferably 50 ppm, and particularly preferably 10 ppm because the conversion of the raw material compound can be further increased, and the target compound can be obtained with higher selectivity.

In the present disclosure, the lower limit of the concentration of water is preferably 1 ppm, more preferably 2 ppm, even more preferably 3 ppm, and particularly preferably 5 ppm because the conversion of the raw material compound can be further increased, and the target compound can be obtained with higher selectivity.

In the present disclosure, the dehydrofluorination reaction is considered to proceed because the Lewis acid site on the surface of the metal catalyst becomes the active site. By carrying out the dehydrofluorination reaction in the gas phase in the presence of water, water is adsorbed on the Lewis acid site on the surface of the metal catalyst. It is presumed that by setting the concentration of water to less than 500 ppm relative to the fluorocarbon represented by formula (2), the Lewis acid site on the surface of the metal catalyst is crushed, and a structure similar to a Bronsted acid site is formed, and thus a decrease in the activity of the metal catalyst is suppressed.

Target Compound

The target compound in the present disclosure is fluoroolefin represented by formula (1): $CX^1X^2\!=\!CX^3X^4$, wherein $X^1$, $X^2$, $X^3$, and $X^4$ are as defined above.

The fluoroolefin represented by formula (1) is at least one member selected from the group consisting of 1,2-difluoroethylene (HFO-1132), 1,1-difluoroethylene (HFO-1132a), and trifluoroethylene (HFO-1123). Of these, HFO-1132 is more preferable.

In the present disclosure, the combination of the raw material compound and the target compound is as follows.

When HFC-143 is used as the raw material compound, HFO-1132 can be obtained as the target compound through a dehydrofluorination reaction.

When HFC-143a is used as the raw material compound, HFO-1132a can be obtained as the target compound through a dehydrofluorination reaction.

When HFC-134 is used as the raw material Compound, HFO-1123 can be obtained as the target compound through a dehydrofluorination reaction.

When HFC-134a is used as the raw material compound, HFO-1123 can be obtained as the target compound through a dehydrofluorination reaction.

RFD-1132 contains trans-1,2-difluoroethylene [(E)-HFO-1132], and cis-1,2-difluoroethylene [(Z)-HFO-1132]; however, in the present disclosure, (Z)-HFO-1132 is preferable.

In the present disclosure, because of activation of the transition site, the isomer ratio of HFO-1132 can be easily maintained to a constant value by performing the dehydrofluorination step in a gas phase in the presence of oxygen.

The isomer ratio of HFO-1132 in the present disclosure can be measured by gas chromatography. The isomer ratio can be changed by varying the dehydrofluorination reaction conditions (temperature, pressure).

In the present disclosure, it is presumed that since the composition ratio of (Z)-HFO-1132 and (E)-HFO-1132 depends on thermodynamic stability, and (Z)-HFO-1132 is more thermodynamically stable than (E)-HFO-1132, the yield of (Z)-HFO-1132 in the target compound is increased.

In the present disclosure, when (2)-HFO-1132 is desired, (E)-HFO-1132:(Z)-HFO-1132 is preferably 1:5, more preferably 1:10, and even more preferably 1:20 in terms of yield.

In the present disclosure, when (E)-HFO-1132 is desired, (E)-HFO-1132:(Z)-HFO-1132 is preferably 1:4, more preferably 1:3, and even more preferably 1:2 in terms of yield.

Precursor of Raw Material Compound

The present disclosure preferably includes a hydrogenation step of subjecting fluoroolefin (also referred to as the precursor of the raw material compound in the present disclosure; the precursor of the raw material compound is referred to below as the "precursor") represented by formula (3): $CX^5X^6\!=\!CX^7X^8$, wherein $X^5$, $X^6$, $X^7$, and $X^8$ are the same or different, and represent a hydrogen atom, a fluorine atom, or a chlorine atom; and at least one of $X^5$, $X^6$, $X^7$, and $X^8$ is a fluorine atom, to a hydrogenation reaction to obtain a raw material compound.

In the present disclosure, the fluoroolefin represented by formula (1) and the fluoroolefin represented by formula (3) are not the same compound.

The precursor is preferably chlorotrifluoroethylene (CTFE).

The method for producing fluoroolefin represented by formula (1): $CX^1X^2\!=\!CX^3X^4$ (wherein, $X^1$, $X^2$, $X^3$, and $X^4$ are the same or different, and represent a hydrogen atom or a fluorine atom, with a proviso that at least one of $X^1$, $X^2$, $X^3$, and $X^4$ is a fluorine atom) according to the present disclosure preferably includes (i) a hydrogenation step of subjecting the fluoroolefin represented by formula (3): $CX^5X^6\!=\!CX^7X^8$, wherein $X^5$, $X^6$, $X^7$ and $X^8$ are the same or different, and represent a hydrogen atom, a fluorine atom, or a chlorine atom; and at least one of $X^5$, $X^6$, $X^7$, and $X^8$ is a fluorine atom, to a hydrogenation reaction to obtain the fluorocarbon represented by formula (2); and (ii) a dehydrofluorination step of bringing the fluorocarbon of formula (2) obtained in the hydrogenation step into contact with a metal catalyst to perform dehydrofluorination.

Hydrogenation Step

In the hydrogenation step in the present disclosure, a known hydrogenation reaction can be used. For example, it is preferable to perform the hydrogenation reaction by supplying a precursor and hydrogen into the reactor in the presence of a reduction catalyst.

As the reduction catalyst, known reduction catalysts can be widely used. For example, those in which a metal, such as Pd, Pt, Rh, Ru, and Rc, is supported on a metal oxide or a metal fluoride, such as activated carbon, and alumina, can be used.

The reaction temperature in the hydrogenation step is usually 30 to 500° C. from the viewpoint of efficiently advancing the hydrogenation reaction.

The shape and the structure of the reactor used in the hydrogenation step are not limited as long as the reactor can withstand the above temperature and pressure. Examples of the reactor include vertical reactors, horizontal reactors, multi-tube reactors, and the like. Examples of materials for the reactor include glass, stainless steel, iron, nickel, iron-nickel alloys, and the like.

Regarding the time of the hydrogenation reaction, from the viewpoint of improving the conversion of the precursor, the contact time ($W/F_0$ of the precursor and the reduction catalyst (W: the reduction catalyst amount (g); $F_0$: the flow rate of the precursor supplied to the reactor (mL/sec)) is usually 0.5 g·sec/mL to 40 g·sec/mL.

The supply molar ratio of hydrogen and a precursor supplied to a reactor in the hydrogenation step (hydrogen supply amount (mL/min)/precursor supply amount (mL/rain)) is usually 2 to 10 in terms of yield.

In the present disclosure, when CTFE is used as a precursor, HFC-143 can be obtained as a raw material compound through a hydrogenation reaction.

EXAMPLES

The present disclosure will be specifically described below with reference to Examples, Comparative Examples, and Reference Examples. However, the present disclosure is not limited to these Examples.

Example 1

SUS piping (outer diameter: ½ inch) was filled with 10 g of chromium oxide mainly containing $Cr_2O_3$ as a catalyst. As a pretreatment for using the catalyst in a dehydrofluorination reaction, anhydrous hydrogen fluoride was passed through the reactor, and a fluorination treatment was conducted by setting the temperature of the reactor to 300 to 460° C. The fluorinated chromium oxide was taken out and used in the dehydrofluorination reaction. The BET specific surface area of the fluorinated chromium oxide was 75 $m^2/g$.

10 g of fluorinated chromium oxide (fluorinated chromium oxide) was added as a metal catalyst to SUS piping (outer diameter: ½ inch), which was a reactor. After drying for 2 hours under nitrogen atmosphere at 200° C., HFC-143 was passed through the reactor as a raw material compound in such a manner that the pressure was atmospheric pressure and the contact time ($W/F_0$) between HFC-143 and the fluorinated chromium oxide was 40 g·sec/mL.

The concentration of water in the raw material compound was measured using a Karl Fischer moisture analyzer (produced by Mitsubishi Chemical Analytic Tech Co., Ltd., trade name CA-200 trace moisture measurement device), and was 10 ppm.

Further, oxygen was added to the reactor in such a manner that the concentration of oxygen was 15 mol % relative to HFC-143, and heating was performed at 350° C. to start a dehydrofluorination reaction.

One hour after the start of the dehydrofluorination reaction, the distillate that passed through a scrubber was collected. Thereafter, mass spectrometry was performed according to the gas chromatography/mass spectrometry (GC/MS) method by using a gas chromatography device (produced by Shimadzu Corporation; trade name: GC-2014), and structural analysis according to NMR spectroscopy was performed using an NMR device (produced by JOEL; trade name: 400YH).

The results of the mass spectrometry and structural analysis confirmed the generation of (E)-HFO-1132 and (Z)-HFO-1132.

The conversion of HFC-143 was 68 mol %. The total yield (selectivity) of (E)-HFC-1132 and (Z)-HFO-1132 was 91 mol %. The selectivity of (E)-HFO-1132 was 18 mol %, and the selectivity of (Z)-HFO-1132 was 73 mol %. The results are shown in Table 1 below.

Example 2

A dehydrofluorination reaction, mass spectrometry, and structural analysis were performed in the same manner as in Example 1 except that the concentration of water in HFC-143 when measured with a Karl Fischer moisture analyzer was 300 ppm. The results are shown in Table 1 below.

Comparative Example 1

SUS piping (outer diameter: ½ inch) was filled with 10 g of chromium oxide mainly containing $Cr_2O_3$ as a catalyst. As a pretreatment for using the catalyst in a dehydrofluorination reaction, anhydrous hydrogen fluoride was passed through the reactor, and a fluorination treatment was conducted by setting the temperature of the reactor to 300 to 460° C. The fluorinated chromium oxide was taken out and used in the dehydrofluorination reaction. The BET specific surface area of the fluorinated chromium oxide was 75 $m^2/g$.

10 g of fluorinated chromium oxide (fluorinated chromium oxide) was added as a metal catalyst to SUS piping (outer diameter: ½ inch), which was a reactor. After drying for 2 hours under nitrogen atmosphere at 200° C., HFC-143 was passed through the reactor as the raw material compound in such a manner that the pressure was atmospheric pressure and the contact time ($W/F_0$) between HFC-143 and fluorinated chromium oxide was 40 g·sec/mL.

The concentration of water in the raw material compound was measured with a Karl Fischer moisture analyzer, and was 500 ppm.

Further, oxygen was added as an oxidizing agent to the reactor in such a manner that the concentration of oxygen was 15 mol % relative to HFC-143, and heating was performed at 350° C. to start a dehydrofluorination reaction.

One hour after the start of the dehydrofluorination reaction, the distillate passed through a scrubber was collected. Thereafter, mass spectrometry was performed according to the gas chromatography/mass spectrometry (GC/MS) method by using a gas chromatography device (produced by Shimadzu Corporation; trade name: GC-2014), and structural analysis according to NMR spectroscopy was performed using an NMR device (produced by JEOL; trade name: 400YH).

The results of the mass spectrometry and structural analysis confirmed the generation of (E)-HFO-1132 and (Z)-HFO-1132.

The conversion of HFC-143 was 42 mol %. The total yield (selectivity) of (E)-HFO-1132 and (Z)-HFO-1132 was 89 mol %. The selectivity of (E)-HFO-1132 was 8 mol %, and the selectivity of (Z)-HFO-1132 was 81 mol %. The results are shown in Table 1 below.

Example 3

A dehydrofluorination reaction, mass spectrometry, and structural analysis were performed in the same manner as in Example 1 except that the concentration of water in HFC-143 when measured with a Karl Fischer moisture analyzer was 10 ppm, and fluorinated chromium oxide, which was a metal catalyst, was dried under nitrogen atmosphere at 400° C. for 2 hours. The results are shown in Table 1 below.

Example 4

A dehydrofluorination reaction, mass spectrometry, and structural analysis were performed in the same manner as in Example 1 except that the concentration of oxygen was set to 0 mol % relative to HFC-143, and the reaction temperature when the dehydrofluorination reaction was started was set to 400° C. The results are shown in Table 2 below.

Example 5

The dehydrofluorination reaction was continuously performed from Example 4, and 3 hours after the start of the dehydrofluorination reaction, mass spectrometry and structural analysis were performed in the same manner as in Example 1. The results are shown in Table 2 below.

Example 6

The dehydrofluorination reaction was continuously performed from Example 4, and 10 hours after the start of the dehydrofluorination reaction, mass spectrometry and structural analysis were performed in the same manner as in Example 1. The results are shown in Table 2 below.

Example 7

A dehydrofluorination reaction, mass spectrometry, and structural analysis were performed in the same manner as in Example 1 except that the reaction temperature when the dehydrofluorination reaction was started was changed to 400° C. The results are shown in Table 2 below.

Example 8

The dehydrofluorination reaction was continuously performed from Example 7, and 3 hours after the start of the dehydrofluorination reaction, mass spectrometry and structural analysis were performed in the same manner as in Example 1. The results are shown in Table 2 below.

Example 9

The dehydrofluorination reaction was continuously performed from Example 7, and 10 hours after the start of the dehydrofluorination reaction, mass spectrometry and structural analysis were performed in the same manner as in Example 1. The results are shown in Table 2 below.

Example 10

A dehydrofluorination reaction, mass spectrometry, and structural analysis were performed in the same manner as in Example 1 except that the concentration of oxygen was set to 0 mol % relative to HFC-143. The results are shown in Table 3 below.

Example 11

SUS piping (outer diameter: ½ inch) was filled with 10 g of chromium oxide mainly containing $Cr_2O_3$ calcined at 700° C. or more as a catalyst. As a pretreatment for using the catalyst in a dehydrofluorination reaction, anhydrous hydrogen fluoride was passed through the reactor, and a fluorination treatment was conducted by setting the temperature of the reactor to 300 to 460° C. The fluorinated chromium oxide was taken out and used in the dehydrofluorination reaction. The BET specific surface area of the fluorinated crystallized chromium oxide was 15 $m^2/g$.

A dehydrofluorination reaction, mass spectrometry, and structural analysis were performed in the same manner as in Example 1 except that 10 g of the fluorinated crystallized chromium oxide was used as a metal catalyst, the oxygen concentration was 0 mol % relative to HFC-143, and the reaction temperature when the dehydrofluorination reaction was started was 600° C. The results are shown in Table 3 below.

Example 12

A dehydrofluorination reaction, mass spectrometry, and structural analysis were performed in the same manner as in Example 1 except that 10 g of the fluorinated crystallized chromium oxide prepared in Example 12 was used as a metal catalyst, the oxygen concentration was set to 0 mol % relative to HFC-143, and the reaction temperature when the dehydrofluorination reaction was started was changed to 580° C. The results are shown in Table 3 below.

Example 13

A dehydrofluorination reaction, mass spectrometry, and structural analysis were performed in the same manner as in Example 1 except that 10 g of the fluorinated crystallized chromium oxide prepared in Example 12 was used as a metal catalyst, the oxygen concentration was set to 5 mol % relative to HFC-143, and the reaction temperature when the dehydrofluorination reaction was started was changed to 400° C. The results are shown in Table 3 below.

Example 14

A dehydrofluorination reaction, mass spectrometry, and structural analysis were performed in the same manner as in Example 1 except that 10 g of the fluorinated crystallized chromium oxide prepared in Example 12 was used as a metal catalyst, the oxygen concentration was set to 10 mol % relative to HFC-143, and the reaction temperature when the dehydrofluorination reaction was started was changed to 400° C. The results are shown in Table 3 below.

Example 15

A dehydrofluorination reaction, mass spectrometry, and structural analysis were performed in the same manner as in Example 1 except that 10 g of the fluorinated crystallized chromium oxide prepared in Example 12 was used as a metal catalyst, and the reaction temperature when the dehydrofluorination reaction was started was changed to 400° C. The results are shown in Table 3 below.

Example 16

A dehydrofluorination reaction, mass spectrometry, and structural analysis were performed in the same manner as in Example 1 except that the contact time ($W/F_0$) was 60 g·sec/mL, and the reaction temperature when the dehydrofluorination reaction was started was 400° C. The results are shown in Table 3 below.

Example 17

A dehydrofluorination reaction, mass spectrometry, and structural analysis were performed in the same manner as in Example 1 except that the contact time ($W/F_0$) was 100 g·sec/mL, and the reaction temperature when the dehydrofluorination reaction was started was 400° C. The results are shown in Table 3 below.

Example 18

SUS piping (outer diameter: ½ inch) was filled with 10 g of $Al_2O_3$ (produced by JGC Catalysts and Chemicals Ltd., N612N) as a catalyst. As a pretreatment for using the catalyst in a dehydrofluorination reaction, anhydrous hydrogen fluoride was passed through the reactor, and a fluorination treatment was conducted by setting the temperature of the reactor to 300 to 460° C. The fluorinated aluminum oxide was taken out and used in the dehydrofluorination reaction. The BET specific surface area of fluorinated aluminum oxide was 90 $m^2/g$.

A dehydrofluorination reaction, mass spectrometry, and structural analysis were performed in the same manner as in Example 1 except that 10 g of the fluorinated aluminum oxide was used as a metal catalyst, the oxygen concentration was set to 0 mol % relative to HFC-143, and the reaction temperature when the dehydrofluorination reaction was started was set to 400° C. The results are shown in Table 3 below.

Example 19

10 g of fluorinated chromium oxide (fluorinated chromium oxide) prepared in Example 1 was added as a metal catalyst to SUS piping (outer diameter: ½ inch), which. Was a reactor. After drying for 2 hours under nitrogen atmosphere at 200° C., HFC-134a was passed through the reactor as the raw material compound in such a manner that the pressure was atmospheric pressure and the contact time (W/F$_0$) between HFC-134a and the fluorinated chromium oxide was 60 g·sec/mL.

The concentration of water in the raw material compound was measured with a Karl Fischer moisture analyzer (produced by Mitsubishi Chemical Analytic Tech Co., Ltd.; trade name: CA-200 trace moisture measurement device), and was 10 ppm.

Further, oxygen used as an oxidizing agent was added to the reactor in such a manner that the concentration of oxygen was 15 mol % relative to HFC-134a, and heating was performed at 400° C. to start a dehydrofluorination reaction.

One hour after the start of the dehydrofluorination reaction, the distillate passed through a scrubber was collected. Thereafter, mass spectrometry was performed according to the gas chromatography/mass spectrometry (GC/MS) method by using a gas chromatography device (produced by Shimadzu Corporation; trade name: GC-2014), and structural analysis according to NKR spectroscopy was performed using an NMR device (produced by JEOL; trade name: 400YH). The results of mass spectrometry and structural analysis confirmed generation of HFO-1123.

The conversion of HFC-134a was 53 mol %. The yield (selectivity) of HFO-1123 was 85 mol %. The results are shown in Table 3.

Reference Example 1

CTFE and hydrogen were passed through SUS piping (outer diameter: ½ inch), which was a reactor, and a hydrogenation reaction was performed according to a known method. One hour after the start of the hydrogenation reaction, the distillate passed through a scrubber was collected. Thereafter, mass spectrometry was performed according to the gas chromatography/mass spectrometry (GC/MS) method by using a gas chromatography device (produced by Shimadzu Corporation; trade name: GC-2014), and structural analysis according to NMR spectroscopy was performed using an NMR device (produced by JEOL; trade name: 400YH). The results of mass spectrometry and structural analysis confirmed that HFC-143 was generated by the hydrogenation reaction.

Tables 1 to 3 show the results of the Examples and the Comparative Examples.

In Tables 1 to 3, the contact time (W/F$_0$ means the rate of the raw material gas that is passed through, i.e., the time in which the metal catalyst is in contact with the raw material compound.

The reaction duration (h) in Table 2 means the time from the start of the flow of the raw material gas.

Regarding the oxygen concentration (mol %) in Tables 2 and 3, the expression "n.d." means that the oxygen concentration measured using an oxygen analyzer (produced by Teldyne Co., Ltd.; trade name: 311 Trace Oxygen Analyzer) was less than the detection limit. "n.d." means "not detected."

TABLE 1

| Example/Comparative Example | Concentration of water (ppm) | Amount of metal catalyst (g) | W/F$_0$ (g·sec/mL) | Reaction temperature (° C.) | Oxygen concentration (mol %) | HFC-143 conversion (mol %) | (E)-1132 selectivity (mol %) | (Z)-1132 selectivity (mol %) |
|---|---|---|---|---|---|---|---|---|
| Example1 | 10 | 10 | 40 | 350 | 15 | 68 | 18 | 73 |
| Example2 | 300 | 10 | 40 | 350 | 15 | 50 | 10 | 80 |
| Comparative Example1 | 500 | 10 | 40 | 350 | 15 | 42 | 8 | 81 |
| Example3 | 10 | 10 | 40 | 350 | 15 | 69 | 15 | 77 |

TABLE 2

| Example | Reaction duration (h) | Concentration of water (ppm) | Amount of metal catalyst (g) | W/F$_0$ (g·sec/mL) | Reaction temperature (° C.) | Oxygen concentration (mol %) | HFC-143 conversion (mol %) | (E)-1132 selectivity (mol %) | (Z)-1132 selectivity (mol %) |
|---|---|---|---|---|---|---|---|---|---|
| Example 4 | 1 | 10 | 10 | 40 | 400 | n.d. | 89 | 30 | 60 |
| Example 5 | 3 | 10 | 10 | 40 | 400 | n.d. | 87 | 21 | 75 |
| Example 6 | 10 | 10 | 10 | 40 | 400 | n.d. | 52 | 10 | 88 |
| Example 7 | 1 | 10 | 10 | 40 | 400 | 15 | 89 | 29 | 59 |
| Example 8 | 3 | 10 | 10 | 40 | 400 | 15 | 87 | 27 | 60 |
| Example 9 | 10 | 10 | 10 | 40 | 400 | 15 | 88 | 25 | 66 |

TABLE 3

| Example | Concentration of water (ppm) | Amount of metal catalyst (g) | W/F$_0$ (g·sec/mL) | Reaction temperature (° C.) | Oxygen concentration (mol %) | HFC-143 conversion (mol %) | (E)-1132 selectivity (mol %) | (Z)-1132 selectivity (mol %) |
|---|---|---|---|---|---|---|---|---|
| Example 10 | 10 | 10 | 40 | 350 | n.d. | 68 | 24 | 70 |
| Example 11 | 10 | 10 | 40 | 600 | n.d. | 85 | 27 | 58 |
| Example 12 | 10 | 10 | 40 | 680 | n.d. | 50 | 16 | 69 |
| Example 13 | 10 | 10 | 40 | 400 | 5 | 80 | 13 | 80 |
| Example 14 | 10 | 10 | 40 | 400 | 10 | 84 | 15 | 79 |

TABLE 3-continued

| Example | Concentration of water (ppm) | Amount of metal catalyst (g) | W/F$_0$ (g·sec/mL) | Reaction temperature (°C.) | Oxygen concentration (mol %) | HFC-134a conversion (mol %) | HFO-1123 selectivity (mol %) |
|---|---|---|---|---|---|---|---|
| Example 15 | 10 | 10 | 40 | 400 | 15 | 88 | 19 | 74 |
| Example 16 | 10 | 10 | 60 | 400 | 15 | 93 | 28 | 63 |
| Example 17 | 10 | 10 | 100 | 400 | 15 | 94 | 31 | 58 |
| Example 18 | 10 | 10 | 40 | 400 | n.d. | 84 | 32 | 60 |
| Example 19 | 10 | 10 | 60 | 400 | 15 | | 53 | 85 |

The invention claimed is:

1. A method for producing a fluoroolefin represented by formula (1): $CX^1X^2=CX^3X^4$, wherein $X^1$, $X^2$, $X^3$, and $X^4$ are the same or different, and represent a hydrogen atom or a fluorine atom,
    the method comprising a dehydrofluorination step of bringing a fluorocarbon represented by formula (2): $CX^1X^2FCX^3X^4H$, wherein $X^1$, $X^2$, $X^3$, and $X^4$ are as defined above, into contact with a metal catalyst to perform dehydrofluorination,
    the dehydrofluorination step being performed in the gas phase in the presence of water,
    the concentration of the water being less than 500 ppm relative to the fluorocarbon represented by formula (2).

2. The production method according to claim 1, wherein the fluoroolefin represented by formula (1) is at least one member selected from the group consisting of 1,2-difluoroethylene (HFO-1132), 1,1-difluoroethylene (HFO-1132a), and trifluoroethylene (HFO-1123).

3. The production method according to claim 1, wherein the fluorocarbon represented by formula (2) is at least one member selected from the group consisting of 1,1,1-trifluoroethane (HFC-143a), 1,1,2-trifluoroethane (HFC-143), 1,1,2,2-tetrafluoroethane (HFC-134), and 1,1,1,2-tetrafluoroethane (HFC-134a).

4. The production method according to claim 1, wherein the dehydrofluorination step is performed in the presence of an oxidizing agent.

5. The production method according to claim 4, wherein the oxidizing agent is oxygen.

6. The production method according to claim 5, wherein the concentration of the oxygen is 0.01 to 21 mol % relative to the fluorocarbon represented by formula (2).

7. The production method according to claim 1, wherein the metal catalyst is at least one member selected from the group consisting of chromium oxide, fluorinated chromium oxide, chromium fluoride, aluminum oxide, fluorinated aluminum oxide, aluminum fluoride, iron oxide, fluorinated iron oxide, iron fluoride, nickel oxide, fluorinated nickel oxide, nickel fluoride, magnesium oxide, fluorinated magnesium oxide, and magnesium fluoride.

8. The production method according to claim 1, wherein the dehydrofluorination step is performed at a temperature of 300 to 600° C.

9. The production method according to claim 1, wherein, in the dehydrofluorination step, the contact time (W/F$_0$) between the fluorocarbon represented by formula (2) and the metal catalyst is 10 g·sec/mL to 200 g·sec/mL.

10. The production method according to claim 1, wherein the dehydrofluorination step is performed in the presence of an inert gas and/or hydrogen fluoride.

11. The production method according to claim 10, wherein the dehydrofluorination step is performed in the presence of an inert gas, and the inert gas is at least one member selected from the group consisting of nitrogen, helium, argon, and carbon dioxide.

12. The production method according to claim 1, comprising a hydrogenation step of subjecting a fluoroolefin represented by formula (3):
    $CX^5X^6=CX^7X^8$, wherein $X^5$, $X^6$, $X^7$, and $X^8$ are the same or different, and represent a hydrogen atom, a fluorine atom, or a chlorine atom; and at least one of $X^5$, $X^6$, $X^7$, and $X^8$ represents a fluorine atom, to a hydrogenation reaction to obtain the fluorocarbon represented by formula (2), wherein the fluorocarbon represented by formula (2) is at least one member selected from the group consisting of 1,1,2-trifluoroethane (HFC-143) and 1,1,2,2-tetrafluoroethane (HFC-134).

13. The production method according to claim 12, wherein the fluoroolefin represented by formula (3) is chlorotrifluoroethylene (CTFE).

* * * * *